(12) United States Patent
Gumucio et al.

(10) Patent No.: US 6,217,906 B1
(45) Date of Patent: Apr. 17, 2001

(54) SELF ADJUSTABLE EXIT PORT

(75) Inventors: Juan C. Gumucio, Santa Clara, CA (US); Keith E. Dionne, Cambridge, MA (US); James E. Brown, Los Gatos, CA (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/397,507

(22) Filed: Sep. 17, 1999

Related U.S. Application Data

(62) Division of application No. 09/045,944, filed on Mar. 23, 1998, now Pat. No. 5,997,527.
(60) Provisional application No. 60/035,607, filed on Mar. 24, 1997.

(51) Int. Cl.$^7$ .............................. A23K 1/18; A61K 9/48; A61K 9/24; A61K 9/22
(52) U.S. Cl. ..................... 424/473; 424/438; 424/451; 604/892.1
(58) Field of Search .................... 424/473, 451; 604/892.1

(56) References Cited

U.S. PATENT DOCUMENTS

| | | | |
|---|---|---|---|
| 3,732,865 | 5/1973 | Higuchi et al. | 424/489 |
| 4,455,143 | 6/1984 | Theeuwes et al. | 424/422 |
| 4,781,714 * | 11/1988 | Eckenhoff et al. | 604/890.1 |
| 5,034,229 | 7/1991 | Magruder et al. | 424/422 |
| 5,122,128 | 6/1992 | Cardinal et al. | 604/892.1 |
| 5,221,278 | 6/1993 | Linkwitz et al. | 424/422 |
| 5,318,558 | 6/1994 | Linkwitz et al. | 604/892.1 |
| 5,456,679 | 10/1995 | Balaban et al. | 424/438 |
| 5,639,477 * | 6/1997 | Maruyama et al. | 424/473 |
| 5,728,396 | 3/1998 | Peery et al. | 424/457 |
| 5,795,591 | 8/1998 | Lee et al. | 604/890.1 |
| 5,861,166 | 1/1999 | Eckenhoff | 424/422 |

* cited by examiner

*Primary Examiner*—Thurman K. Page
*Assistant Examiner*—S. Tran
(74) *Attorney, Agent, or Firm*—Pauline A. Clarke; Robert G. Mukai; Steven F. Stone

(57) ABSTRACT

A delivery device having a first chamber containing an osmotic agent, a membrane forming a wall of the first chamber through which fluid is imbibed by osmosis, a second chamber containing a beneficial agent to be delivered, and a moveable piston separating the two chambers. In fluid communication with the second chamber is an orifice which comprises a slit valve. In the presence of pressure, the beneficial agent pushes through the slit, opening up a channel for delivery of the beneficial agent and creating flow. Because the slit remains closed in the absence of flow (or when the pressure is below the pressure required to open the slit), back diffusion of external fluids is eliminated when the slit is closed, which prevents contamination of the beneficial agent in the second chamber by external fluids. In addition, forward diffusion of the beneficial agent out of the capsule is prevented when the slit is closed. The slit valve opens only to the minimum dimension required to allow the flow generated by the osmotic pumping rate. The slit valve also allows a flow path to open around any obstruction in the slit valve to prevent clogging.

15 Claims, 7 Drawing Sheets

SELF ADJUSTABLE EXIT PORT

CROSS REFERENCE TO RELATED APPLICATIONS

This application is a divisional of application Ser. No. 09/045,944, filed Mar. 23, 1998, now U.S. Pat. No. 5,997,527, which claims the benefit of U.S. Provisional Application No. 60/035,607, filed Mar. 24, 1997, pursuant to 35 U.S.C. §119(e).

BACKGROUND OF THE INVENTION

1. Field of the Invention

The present invention relates generally to an implantable delivery device, and more particularly to an exit port, such as a slit orifice for an implantable osmotic delivery device which has a variable size.

2. Description of the Related Art

Controlled delivery of beneficial agents such as drugs in the medical and veterinary fields has been accomplished by a variety of methods. One approach for delivering a beneficial agent involves the use of implantable diffusional systems. For example, subdermal implants for contraception are described by Philip D. Darney in *Current Opinion in Obstetrics and Gynecology*, 1991, 3:470–476. Norplant® requires the placement of 6 levonorgestrel-filled silastic capsules under the skin. Protection from conception for up to 5 years is achieved. The implants operate by simple diffusion, that is, the active agent diffuses through the polymeric material at a rate that is controlled by the characteristics of the active agent formulation and the polymeric material.

Another method for controlled prolonged delivery of a beneficial agent involves the use of an implantable osmotic delivery system. Osmotic delivery systems are very reliable in delivering the beneficial agent over an extended period of time. The osmotic pressure generated by an osmotic pump also produces a delivery rate of the beneficial agent into the body which is relatively constant as compared with other types of delivery systems.

In general, osmotic delivery systems operate by imbibing fluid from the outside environment and releasing corresponding amounts of the beneficial agent. Osmotic delivery systems, commonly referred to as "osmotic pumps", generally include some type of a capsule having walls which selectively pass water into an interior of the capsule which contains a water-attracting agent. The absorption of water by the water-attracting agent within the capsule reservoir creates an osmotic pressure within the capsule which causes the beneficial agent to be delivered from the capsule. The water-attracting agent may be the beneficial agent delivered to the patient, however, in most cases, a separate agent is used specifically for its ability to draw water into the capsule.

When a separate osmotic agent is used, the osmotic agent may be separated from the beneficial agent within the capsule by a movable dividing member or piston. The structure of the capsule is such that the capsule does not expand when the osmotic agent takes in water. As the osmotic agent expands, it causes the movable dividing member or piston to move, which in turn causes the beneficial agent to be discharged through an orifice at the same volumetric rate that water enters the osmotic agent by osmosis.

The orifice controls the interaction of the beneficial agent with the external fluid environment. The orifice serves the important function of isolating the beneficial agent from the external fluid environment, since any contamination of the beneficial agent by external fluids may adversely affect the utility of the beneficial agent. For example, the inward flux of materials of the external fluid environment due to diffusion or osmosis may contaminate the interior of the capsule, destabilizing, diluting, or otherwise altering the beneficial agent formulation. Another important function of the orifice is to control or limit diffusional flow of the beneficial agent through the orifice into the external fluid environment.

In known delivery devices, these functions have typically been performed by flow moderators. A flow moderator may consist of a tubular passage having a particular cross sectional area and length. The cross sectional area and length of the flow moderator is chosen such that the average linear velocity of the exiting beneficial agent is higher than that of the linear inward flux of materials in the external environment due to diffusion or osmosis, thereby attenuating or moderating back diffusion and its deleterious effects of contaminating the interior of the osmotic pump.

In addition, the dimensions of the flow moderator may be chosen such that the diffusive flux of the beneficial agent out of the orifice is small in comparison to the convective flux. FIG. 1 is a graph showing the relationship between the orifice dimensions and drug diffusion as a percentage of pumped or connective delivery for one set of pumping rates and drug diffusivity. FIG. 1 shows, for example, that the diffusive flux of the beneficial agent can be kept to less than 10% of the convective flow using an orifice having a diameter of 5 mils and a length of at least 0.6 cm, or an orifice having a diameter of 10 mils and a length of at least 2.4 cm.

One problem with flow moderators, however, is that the passage may become clogged or obstructed with particles suspended in the beneficial agent or in fluid from the external environment. Such clogging may be reduced or eliminated by increasing the diameter of the passage to 5 mil or more, for example. However, as shown in FIG. 1, this increase results in a greater rate of diffusion of the beneficial agent out of the osmotic pump. A corresponding increase also occurs in the back diffusion of the external fluid into the osmotic pump which may contaminate the beneficial agent and adversely affect the desired delivery rate of the beneficial agent. Tolerances during fabrication also frequently dictate that the orifice diameter be greater than about 5 mils.

Systems with a long straight flow moderator are also impractical for implantation applications because they increase the size of the implant significantly making the system difficult to implant.

Current flow modulators also cause separation of beneficial agents which contain suspensions of bioactive macromolecules (proteins, genes, etc.). When such suspensions pass along a restriction in current flow modulators, the suspension separates and the delivery concentration of bioactive macromolecules varies.

SUMMARY OF THE INVENTION

According to one embodiment of the invention, an exemplary delivery device, such as described in U.S. patent application Ser. No. 08/595,761, the entire disclosure of which is incorporated herein by reference, may be provided with the slit orifice of the present invention. The delivery device comprises a capsule containing a beneficial agent and an osmotic agent, a membrane which forms a portion of a wall of the capsule, the membrane allowing fluid from an external environment to pass into the capsule by osmosis to create an osmotic pressure in the capsule, means for applying the osmotic pressure to the beneficial agent, and a flexible member having therein a slit orifice which is in fluid communication with the capsule.

In the presence of flow, the beneficial agent pushes through the slit, opening up a channel for delivery of the beneficial agent. Because the slit orifice remains closed in the absence of flow, back diffusion of external fluids is eliminated when the slit is closed, which prevents contamination of the beneficial agent by external fluids. Forward diffusion of the beneficial agent out of the capsule is also prevented.

In addition, the slit orifice allows a flow path to open around an obstruction in the slit orifice. In the event that a suspended particle becomes lodged in the slit orifice, a new flow path is created around the obstacle, thereby preventing clogging. The slit orifice is also very compact and easily fits inside the delivery device, which is advantageous when the delivery device is implanted subcutaneously.

This combination uniquely addresses the complex issues presented in the extremely low flow, high osmolar drug delivery systems as found, for example, in U.S. patent application Ser. No. 08/595,761 which has been converted to Provisional Application No. 60,122,056. These issues drug diffusion out of the orifice, back diffusion of liquid from the environment of use into the orifice, and clogging of the orifice, especially if the orifice is small enough to eliminate drug diffusion and back diffusion.

BRIEF DESCRIPTION OF THE DRAWINGS

The foregoing and other objects, features and advantages of the present invention will be more readily understood upon reading the following detailed description in conjunction with the drawings in which.

DESCRIPTION OF THE PREFERRED EMBODIMENTS

Definitions

The term "beneficial agent" includes any physiologically or pharmacologically active substance or substances option-ally in combination with pharmaceutically acceptable carriers and optionally additional ingredients such as antioxidants, stabilizing agents, permeation enhancers, etc.

The term "impermeable" refers to a material that is sufficiently impermeable to environmental fluids as well as ingredients contained within the dispensing device such that the migration of such materials into or out of the device through the impermeable material is so low as to have substantially no adverse impact on the function of the device.

The term "semipermeable" refers to a material that is permeable to external fluids but substantially impermeable to other ingredients contained within the dispensing device and the environment of use.

Water-attracting agents which are used to drive the osmotic flow of an osmotic delivery device are referred to herein as "osmotic agents."

Figure 2:
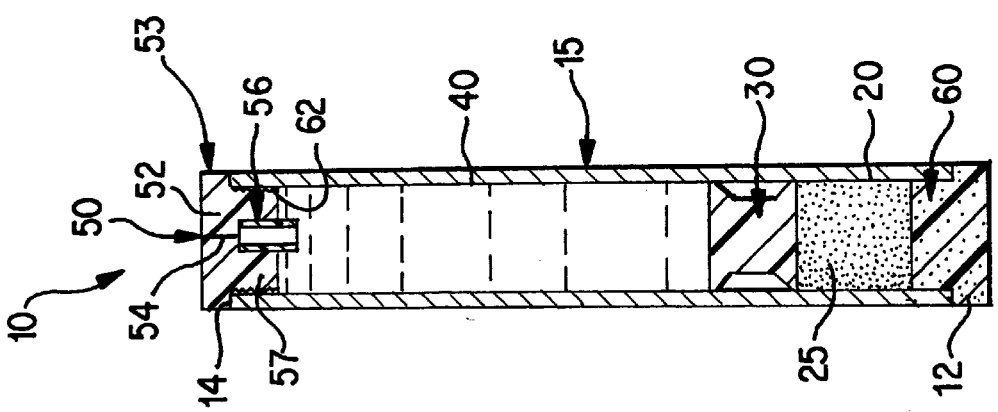
FIG. 2 illustrates a delivery device which includes a slit orifice according to an exemplary embodiment of the invention.

FIG. 2 illustrates an example of an osmotic delivery device 10 according to an exemplary embodiment of the present invention. The osmotic delivery device 10 generally includes a first chamber 20, a piston 30, and a second chamber or reservoir 40, all of which may be enclosed within an elongated substantially cylindrical capsule 15. The elongated capsule 15 is formed of a material such as titanium which is sufficiently rigid to withstand expansion of an osmotic agent without changing size or shape. The elongated capsule 15 is impermeable to fluids and gases in the environment and to the ingredients contained therein.

The first chamber 20 contains an osmotic agent 25 which attracts water and which may be in the form of a tablet. The osmotic agent 25 may be, for example, a non-volatile water soluble osmagent, an osmopolymer which swells upon contact with water, or a mixture of the two. The second chamber 40 contains a beneficial agent, such as a drug, to be delivered. The second chamber 40 is separated from the first chamber 20 by a movable piston 30. The movable piston 30 is a substantially cylindrical member which is configured to fit within the capsule 15 in a sealed manner and to slide along a longitudinal axis within the capsule. The piston 30 preferably is formed of an impermeable resilient material which forms a seal with the walls of the capsule 15.

The drug delivery device 10 at its inlet end 12 includes a membrane 60 which forms at least a portion of a wall of the first chamber 20. The membrane 60 is formed of a semipermeable material which allows fluid to pass from an exterior fluid environment into the first chamber 20 by osmosis to cause the osmotic agent to swell. The membrane 60 may be in the form of a semipermeable plug which is inserted in an open end 12 of the capsule 15 as shown in FIG. 2. The membrane 60 is impermeable to the materials within the first chamber 20 so that they do not flow out of the capsule 15 through the membrane 60.

Materials from which the membrane 60 can be made are those that are semipermeable and that can conform to the shape of the capsule 15 upon wetting and adhere to the rigid surface of the capsule 15. The membrane 60 expands as it hydrates so that a seal is generated between the surface of the membrane 60 and the capsule 15. The materials from which the membrane 60 is made vary based on desired pumping rates and device configuration requirements and include, but are not limited to, plasticized cellulosic materials, enhanced polymethylmethacrylates such as hydroxyethylmethacrylate (HEMA) and elastomeric materials such as polyurethanes and polyamides, polyetherpolyamide copolymers, thermoplastic copolyesters and the like.

In operation, when the delivery device 10 is situated in an aqueous environment, water is drawn through the membrane 60 by osmosis into the first chamber 20 containing the osmotic agent. The osmotic agent swells, creating an osmotic pressure in the first chamber 20 which is applied to the second chamber 40 via the piston 30. The piston slides away from the membrane 60 forcing the beneficial agent in the second chamber 40 to be delivered through at least one orifice 50 in the second chamber. The osmotic pump provides a relatively constant rate of water intake which can be used to reliably deliver a desired quantity of the beneficial agent over time.

The orifice 50, according to one embodiment of the invention, is formed in a plug 52 of an elastic or semi-elastic material such as silicone, rubber, santoprene, polyurethane, or an elastomeric thermoplastic polymer such as C-FLEX. The plug 52 is retained in an outlet end 14 of the capsule 15. The orifice 50 comprises a slit 54 made through the elastic or semi-elastic plug 52 which may be fluidly connected to a flow moderator 56 disposed in the plug 52. The slit 54 and flow moderator 56 fluidly connect the interior of the second chamber 40 to the external fluid environment.

As shown in FIG. 2, the plug 52 may have two sections. The first section 57 has an outer diameter which is small enough to allow the plug 52 to be inserted into the outlet end 14 of the capsule 15. The flow moderator 56 is disposed in the first section 57. The second section 53 contains at least a portion of the slit 54 and extends beyond the outlet end 14 of the capsule 15.

The orifice 50 operates as a valve which opens under the pressure of the beneficial agent. The slit 54 of the orifice 50 may be under slight compression, for example from compressive forces which form a seal between the outside of the plug 52 and the inside of the reservoir 15, so that in the absence of flow, the slit 54 forms a closed valve which prevents fluid flow in either direction. Alternatively, the materials used and plug dimensions may be selected so that the slit seals or closes without the need for external compression. The slit 54 is preferably formed in the second section 53 of the plug 52 which extends beyond the capsule 15 so that the walls of the capsule 15 do not exert a significant closing force on the slit 54.

In the presence of flow, the beneficial agent pushes through the slit 54, opening up a channel for delivery of the beneficial agent. In the absence of flow, the slit 54 remains closed. When the slit is closed, back diffusion of external fluids is eliminated, which prevents contamination of the beneficial agent in the second chamber 40 by external fluids. In addition, forward diffusion of the beneficial agent out of the capsule 15 is prevented. In continuous flow osmotic delivery systems, the slit 54 will generally remain open throughout delivery of the beneficial agent. However, pulsatile and bolus type delivery systems will generally cause the slit 54 to close during non-delivery periods.

When the osmotic pressure is high enough to open the slit 54 in the orifice 50, the slit 54 provides a flow channel of variable dimensions. The plug 52 in which the slit 54 resides preferably comprises an elastic or semi-elastic material. The osmotic pressure is great enough to overcome the elasticity of the plug 52 and force open the slit 54. However, because the plug 52 is elastic, the flow channel which is formed is preferably just large enough to allow passage of the beneficial agent therethrough. The flow channel through the slit 54 may assume a range of sizes based on the osmotic pumping rate and the viscosity of the beneficial agent, for example.

The slit 54 generally opens to the smallest required diameter or opening to allow for flow of beneficial agent through it. This is much smaller than could be achieved with a rigid channel due to machining and tolerance limitations and/or particulate clogging of such a small rigid channel.

As will be appreciated by those skilled in the art, the dimensions and composition of the plug 52 and the slit 54 can be adjusted so that the slit 54 forms an orifice of a desired size when used with a particular beneficial agent and osmotic pump. For example, as the length of the slit 54 increases, the size of the orifice created by the slit 54 can increase. Also, as the thickness of the plug 52 along a longitudinal direction of the capsule 15 increases, the plug 52 becomes more resistant to forming an orifice from the slit 54. The composition of the plug 52 also affects the tendency of the slit 54 to open into an orifice. A more elastic material will more easily form an orifice, or may form a wider orifice, than a more rigid material. By varying these properties of the plug 52 and slit 54, the orifice can be configured to open to a desired degree given the parameters of the delivery device, e.g., the viscosity of the beneficial agent, the flow rate of the osmotic pump, and the pressure of the osmotic pump. By varying the parameters listed above, one can achieve an orifice that "opens" at a predetermined internal pressure, e.g. 30 $lbf/in^2$.

Figure 1:
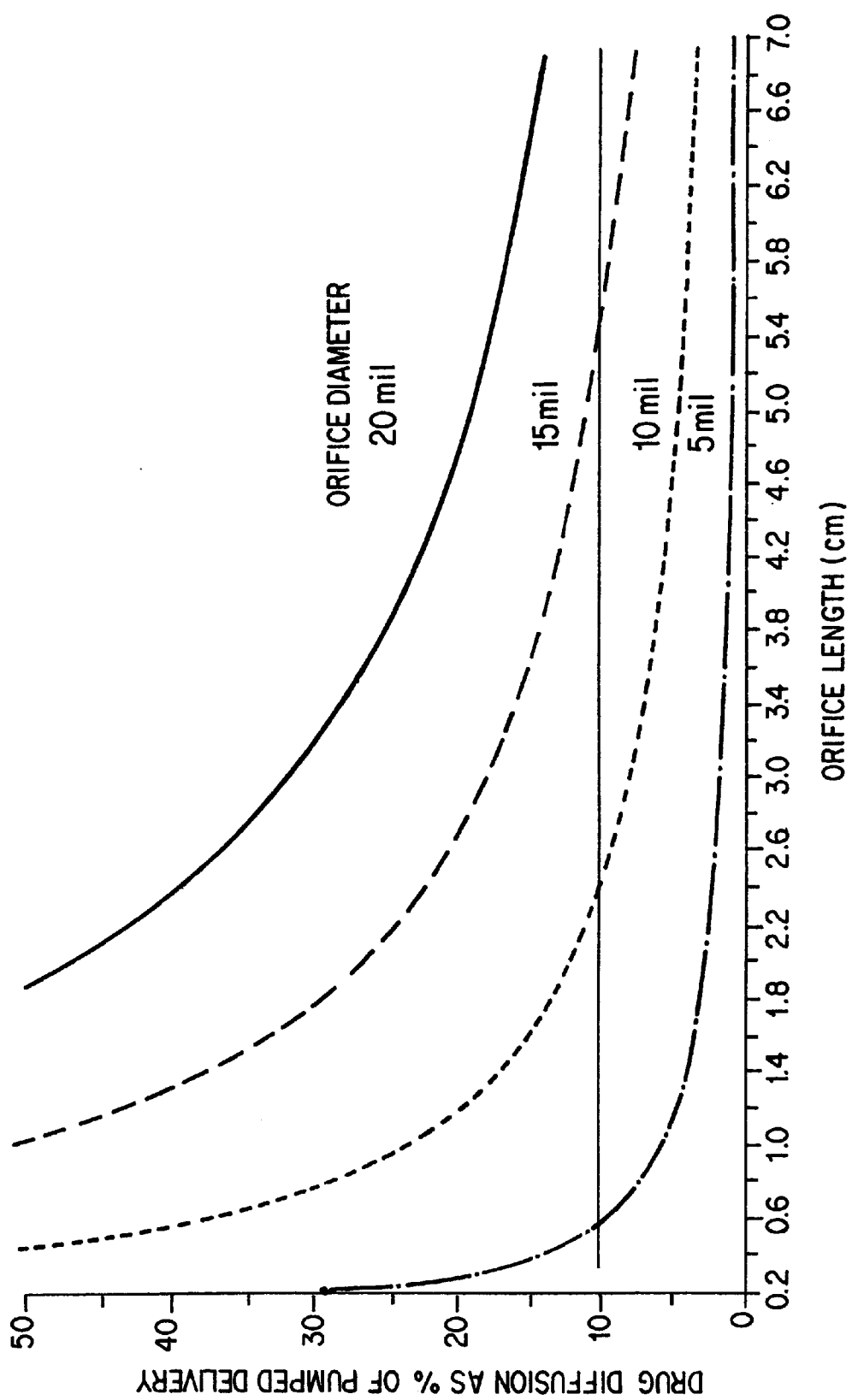
FIG. 1 is a graph of drug diffusion as a function of the diameter and length of the orifice of a delivery device.

The ability to vary the size of the orifice 50 has the advantage that the cross sectional area of the orifice 50 can be made small under the operating conditions of the delivery device, which reduces diffusion of the beneficial agent out of the delivery device, as shown in FIG. 1, and reduces back diffusion of external fluids into the delivery device. Generally, the system is designed so that the slit 54 is forced open to the smallest possible degree to let the formulation seep through its opening.

In addition, the requirement in prior delivery devices of a fixed dimension orifice of sufficient size to permit passage of micro-aggregates is eliminated because the slit 54 allows a flow path to open around an obstruction in the orifice 50. In the event that a suspended particle becomes lodged in the orifice 50, a new flow path is created around the obstacle, thereby preventing clogging. In operation, the active flow channel may be significantly smaller than is required in a fixed diameter orifice channel to prevent clogging.

Another advantage of the orifice 50 shown in FIG. 2 is that the orifice is very compact and easily fits inside the delivery device 10, as compared with a conventional flow moderator which may be from 2 to 7 cm long, for example. The small size of the orifice 50 is advantageous when the delivery device 10 is implanted subcutaneously.

The flow moderator 56 may comprise a tube formed of a rigid or semi-rigid material such as Teflon, HDPE, LDPE, or a metal, for example. The flow moderator 56 forms a semi-rigid opening and allows compressive pressure to be used to form a seal between the outside of the plug 52 and the inside of the reservoir 15 without compressing the slit 54 shut. Thus, as illustrated in FIG. 2, the slit 54 may be located in the uncompressed second section 53 of the plug 52 such that the slit is not subject to the compression forces which form the seal between the plug 52 and the capsule 15. Likewise, the slit 54 may extend into the first section 57 such that the slit is subject to these compressive forces.

Hence, the flow moderator 56 functions to improve the seal between the plug 52 and the capsule 15. As shown in FIG. 2, the plug 52 may have several sealing ridges 62 which each form a seal between the plug 52 and the capsule 15 to effectively isolate the beneficial agent in the second chamber 40 from the external fluid environment. Because the flow moderator 56 may be formed of a rigid material, it may exert an outward radial force on the plug 52, which is preferably less rigid than the flow moderator 56. This outward radial force increases the pressure exerted by the sealing ridges 62 against the inside of the capsule 15, which improves the seal between the plug 52 and the capsule 15. In addition, the outward radial force increases the resistance of the plug 52 to being pushed out of the capsule 15 by the osmotic pressure generated by the osmotic pump. In other embodiments of the present invention, the outward radial forces may also regulate the flow of the beneficial agent and prevent back diffusion of external fluids into the capsule 15.

According to one exemplary embodiment of the present invention, the slit 54 illustrated in FIG. 2 is formed by inserting a hypodermic needle, pin, or blade through the first and second sections 57, 53 of the plug 52. For example, a hypodermic needle having a predetermined diameter is inserted through the body of the orifice 20 along the center axis of the orifice (parallel with the longitudinal axis of the capsule 15). Thereafter, the needle is removed from the orifice 50. After the slit 54 has been formed in the orifice 50, the flow moderator 56 is inserted into the first section 57 of the plug 52. Depending upon the material of the plug 52, and the dimensions of the slit 54 and flow moderator 56, it may be necessary to drill, carve, punch, or mold a cylindrical recess in the first section 57 to receive the flow moderator. In any case, the flow moderator 56 is preferably positioned within the first section 57, and secured to the first section 57 via an interference fit, although adhesives, threads and other means may be used to secure the flow moderator to the first section of the plug 52. An end of the flow moderator 56 may protrude from the first section 57, may be located within the first section, or may be inserted in the first section such that it is flush with the first section.

The slit 54 may also be formed after the flow moderator 56 has been inserted into the first section 57 of the plug 52. According to this method, the flow moderator 56 is first inserted into the first section 57 of the plug 52. Thereafter, a needle or device for forming the slit 54 is inserted completely through the cylindrical channel of the tubular flow moderator 56 and through the second section 53 of the plug 52 to form the slit.

For example, an orifice 50, such as that illustrated in FIG. 2, may be formed by first inserting a 1.5 mm long portion of a 21 gauge (diameter of approximately 0.8 mm) hypodermic needle into the first section 57 of a plug 52 of styrene ethylene butadiene styrene block copolymer (C-FLEX LS 55A, commercially available from CONSOLIDATED POLYMER TECHNOLOGIES). The 1.5 mm long portion of the 21 gauge hypodermic needle is preferably at least half the length of the final slit 54 to be formed. The following dimensions of the plug 52 and capsule 15 are also preferred for this example: (1) the C-FLEX plug 52 is approximately 3.85 mm long (measured on an axis parallel with the longitudinal axis of the capsule into which the orifice 50 is to be inserted), although only 3.13 mm of the plug is inserted into the capsule 15 after the orifice 50 has been fabricated; (2) the plug 52 includes four equally spaced sealing ridges 62, each having an outer diameter of approximately 3.24 mm and each approximately 0.26 mm thick (measured on an axis parallel with the longitudinal axis of the capsule into which the orifice 50 is to be inserted); (3) the diameter of the cylindrical body of the plug 52 at the base of the sealing ridges 62 is approximately 2.98 mm; and (4) the inner diameter of the capsule 15 that receives the plug 52 is approximately 3.0 mm.

After the 1.5 mm long portion of the 21 gauge hypodermic needle has been inserted into the first section 57 of the plug 52, a second hypodermic needle having a smaller diameter than the portion of the 21 gauge hypodermic needle is inserted into the portion of the 21 gauge hypodermic needle and completely through the first and second sections 57, 53 of the plug 52. This step forms the slit 54, and also removes any plug material inside the portion of the 21 gauge hypodermic needle to form the flow moderator 56. If the second hypodermic needle is sized to tightly fit through the 21 gauge flow moderator 56, the resulting slit 54 will be approximately 0.4 mm wide as measured perpendicular to the center axis of the orifice 50. An orifice 50 having the above dimensions is intended to be particularly useful for delivering high viscosity formulations of beneficial agents, such as 3% sodium carboxymethyl cellulose in water.

Figure 9:
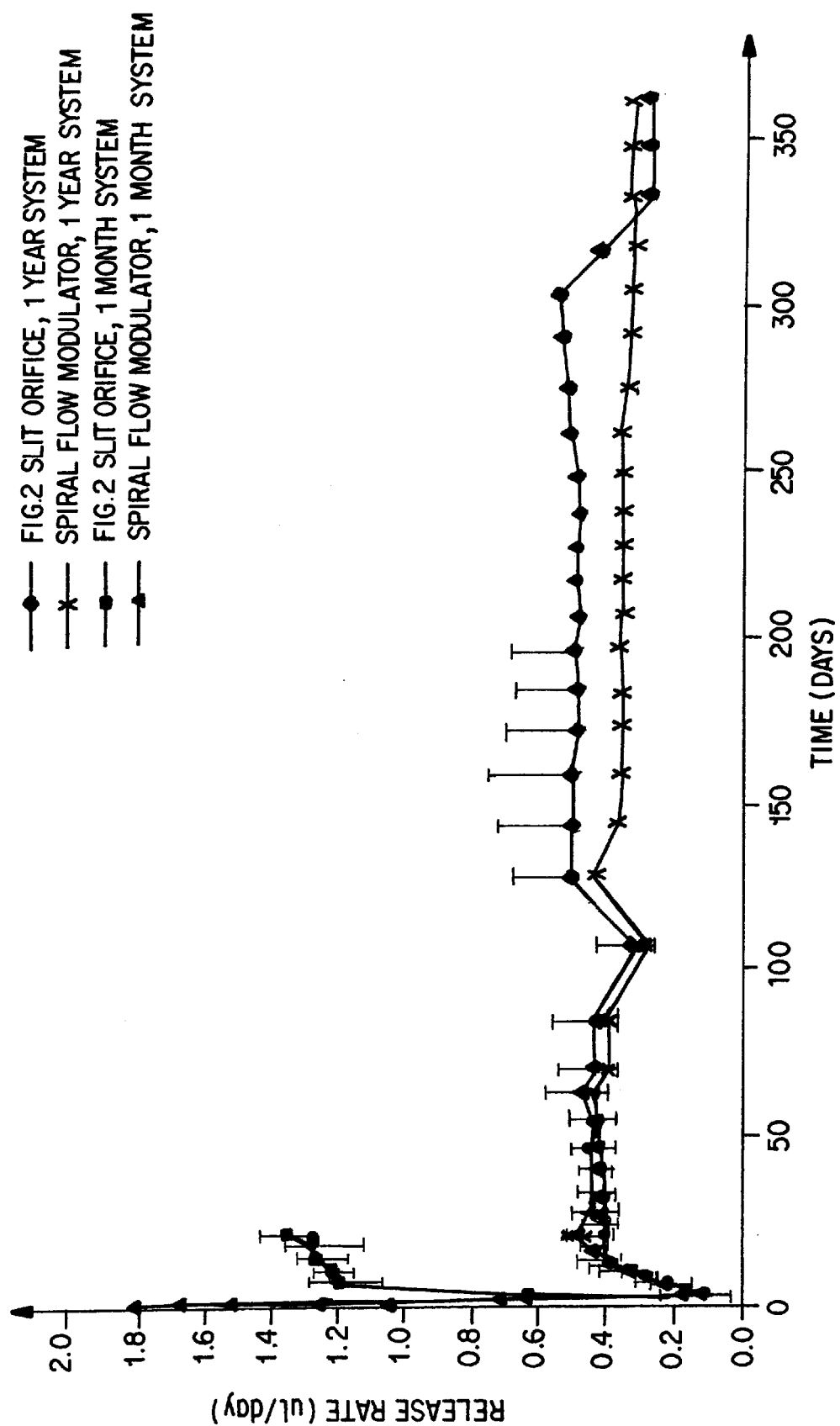
FIG. 9 is a graph illustrating a comparison of the release rates of two osmotic delivery devices having an orifice according to one embodiment of the present invention with the release rates of two osmotic delivery devices having a spiral flow moderator.

FIG. 9 is a graph of the release rate of beneficial agent over time and compares two osmotic delivery systems having a spiral flow moderator with two osmotic delivery systems or devices 10 having an orifice 50 according to embodiments of the present invention, such as that illustrated in FIG. 2. The osmotic delivery devices 10 tested in FIG. 9 included the capsule 15 and orifice 50 dimensioned and described above having the C-FLEX LS 55A plug 52 with the 0.4 mm slit 54 and the 21 gauge flow moderator 56.

As illustrated in FIG. 9, the two osmotic delivery systems having a spiral flow moderator and the two osmotic delivery systems 10 having the orifice 50 according to embodiments of the present invention were tested. The respective systems were configured to deliver a beneficial agent, in this case water with blue dye, over a one month and one year time period.

The osmotic delivery system 10 according to the present invention that was configured to deliver the beneficial agent over a one year time period delivered approximately 0.4 uL/day of the beneficial agent. Comparatively, the osmotic delivery system incorporating the spiral flow modulator and configured to deliver the beneficial agent over a one year time period also delivered approximately 0.4 uL/day of the beneficial agent. Thus, FIG. 9 illustrates that the osmotic delivery system 10 incorporating the orifice 50 and configured to deliver the beneficial agent over a one year time period performed as well as the osmotic delivery system incorporating the spiral flow modulator.

The osmotic delivery system 10 according to the present invention that was configured to deliver the beneficial agent over a one month time period delivered roughly 1.3 uL/day of the beneficial agent. Comparatively, the osmotic delivery system incorporating the spiral flow modulator and configured to deliver the beneficial agent over a one month time period also delivered roughly 1.3 uL/day of the beneficial agent. Thus, FIG. 9 illustrates that the osmotic delivery system 10 incorporating the orifice 50 and configured to deliver the beneficial agent over a one month time period performed as well as the osmotic delivery system incorporating the spiral flow modulator. In sum, the results depicted in FIG. 9 illustrate that the tested orifices 50 were as effective as the spiral flow moderators in delivering a beneficial agent at different release rates.

Figure 3:
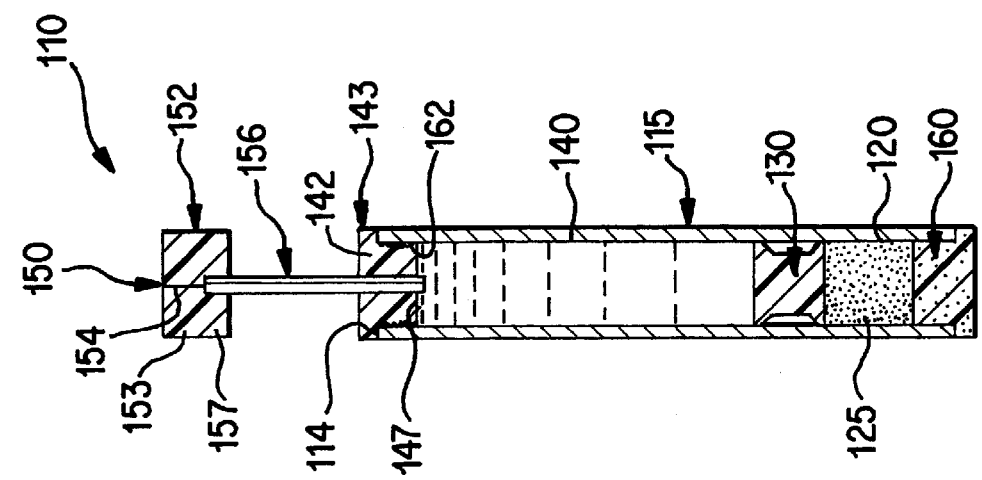
FIG. 3 illustrates a delivery device which includes a slit orifice and a catheter according to another embodiment of the invention.

FIG. 3 illustrates another embodiment of the invention in which a catheter 156 is provided in fluid communication between the slit 154 and the capsule 115. As shown in FIG. 3, the delivery device 110 includes a membrane 160 which may be in the form of a diffusion plug, a first chamber 120 which contains an osmotic agent 125, a second chamber 140 which contains a beneficial agent, and a moveable piston 130 which separates the first chamber 120 from the second chamber 140. The osmotic pump, including the first and second chambers, piston, and membrane, functions in the same manner as the pump of FIG. 2.

As shown in FIG. 3, the delivery device 110 includes a plug 142 having a catheter 156 fixed therein. The plug 142 fits in the outlet end 114 of the capsule 115 and may include a plurality of ridges 162 to seal the plug 142 to the capsule 115. The plug 142 may have a first portion 147 which fits inside the walls of the capsule 115 and a second portion 143 which extends beyond the outlet end 114 of the capsule 115. The plug 142 may be formed of an elastic or semi-elastic material such as silicone, rubber, santoprene, polyurethane, etc.

The catheter 156 is disposed in the plug 142 and is in fluid communication with the beneficial agent in the second chamber 140. The catheter 156 is preferably formed of a rigid or semi-rigid material such as Teflon, HDPE, LDPE, or a metal so that it exerts a radially outward force on the plug 142 to increase the pressure of the ridges 162 on the inside wall of the capsule 115. The increased pressure improves the seal between the plug 142 and the capsule 115 and increases the resistance of the plug 142 to being forced out of the capsule 115 by the osmotic pressure generated by the osmotic pump.

The catheter 156 is also in fluid communication with a slit 154 formed in a flexible member 152. The flexible member 152 preferably comprises an elastic or semi-elastic material such as silicone, rubber, santoprene, polyurethane, etc. The flexible member 152 may have two sections, a first section 157 in which the end of the catheter 156 is disposed, and a second section 153 in which the slit 154 is located. The slit 154 functions in much the same manner as the slit 54 of FIG. 2. However, the slit 154 is not subject to compressive forces created by the seal between the plug 142 and the capsule 115.

The slit 154 is designed such that in the absence of flow, the slit 154 forms a closed valve which prevents fluid flow in either direction. In the presence of flow, the beneficial agent pushes through the slit 154, opening up a channel for delivery of the beneficial agent. The dimensions and composition of the flexible member 152 and slit 154 can be chosen so that the slit 154 forms an orifice of a desired size under the operating parameters of the delivery device, e.g., the viscosity of the beneficial agent, the flow rate of the osmotic pump, and the pressure of the osmotic pump.

Because the flexible member 152 is elastic, the flow channel which is formed is preferably just large enough to allow passage of the beneficial agent therethrough. The variability of the size of the orifice has the advantage that the cross sectional area of the orifice is small (e.g., significantly smaller than a flow moderator of fixed diameter), which reduces diffusion of the beneficial agent out of the delivery device, as shown in FIG. 1, and reduces diffusion of external fluids into the delivery device. The slit 154 also allows a flow path to open around an obstruction in the slit 154.

The catheter 156 may have dimensions such that it performs as a flow moderator, if desired, to further reduce diffusion of the beneficial agent out the slit 154 and back diffusion of external fluids into the second chamber 140.

The catheter 156 is also useful when the desired point of delivery of the beneficial agent is difficult to access. For example, it may be advantageous therapeutically to deliver the beneficial agent at a location which cannot accommodate or tolerate the capsule 115. In this situation, the capsule 115 may be implanted in a more acceptable location while the catheter 156 transports the beneficial agent to the slit 154 at the delivery site. This embodiment may also be utilized to make the capsule 115 more accessible to a treating physician rather than being implanted at a location which requires an invasive procedure. For example, the capsule 115 may be implanted close to the surface of the skin while the catheter 156 delivers the beneficial agent to a more remote location.

Figure 4:
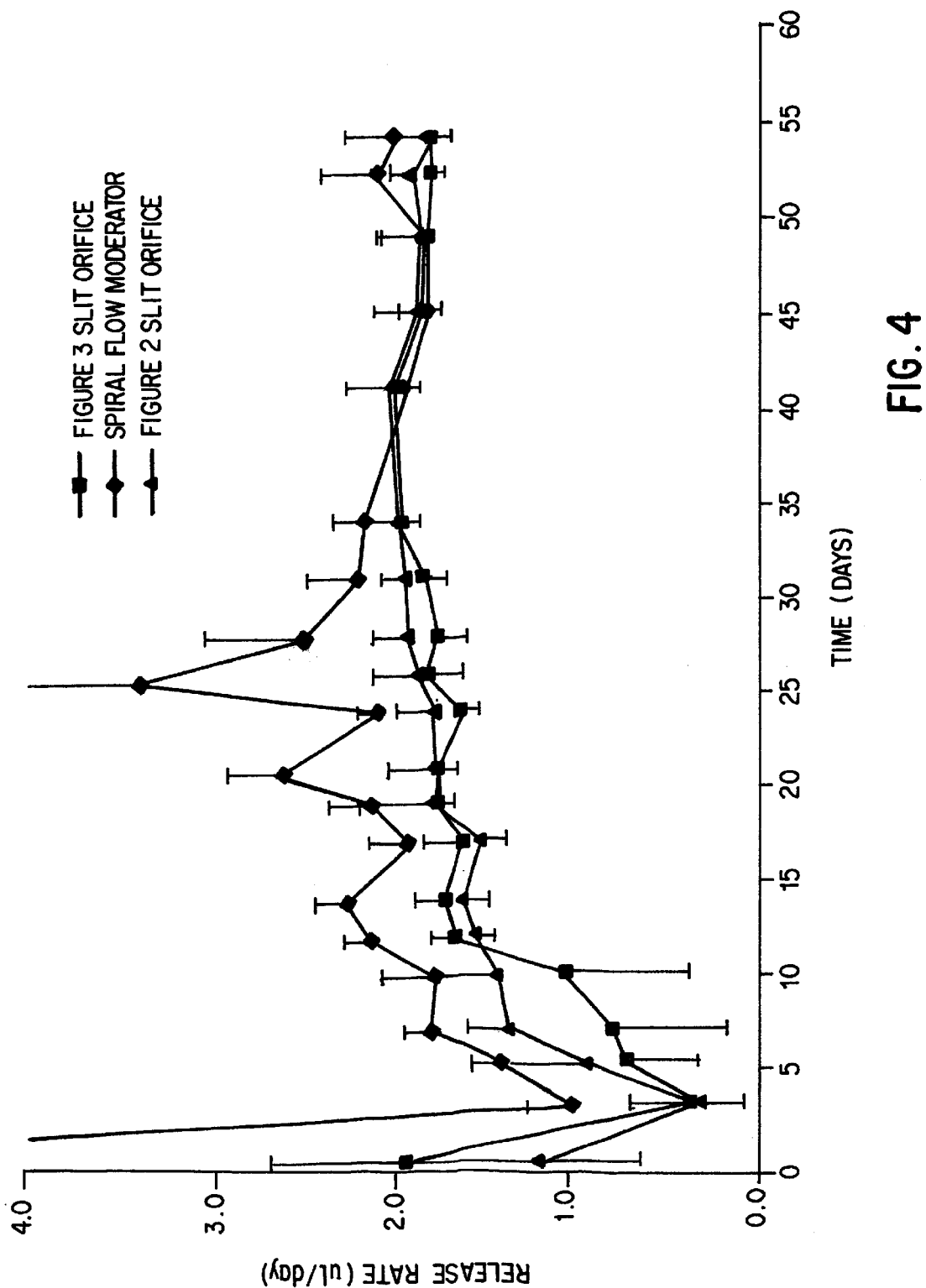
FIG. 4 is a graph which shows the release rates of the delivery devices of FIGS. 2 and 3 as a function of time.

The improved performance of the exemplary delivery devices of FIGS. 2 and 3 is shown in FIG. 4. FIG. 4 is a graph of the release rate in microliters per day over time of the delivery devices of FIGS. 2 and 3. FIG. 4 also shows the release rate of a delivery device having a tubular flow moderator orifice in the shape of a spiral. The data used in FIG. 4 were obtained by placing each delivery device in a release rate bath. The delivery devices were filled with a 1% solution of blue dye in deionized water. At fixed points in time, the concentration of blue dye in the release rate bath was measured. The experiment was conducted five times, and the error bars shown in FIG. 4 represent the standard deviation of the measurements.

The procedure and materials used in obtaining the data shown in FIG. 4 are as follows:

Granulation Tablet Compression:

| | |
|---|---|
| TOWLING: | 0.117" flat face |
| GRANULATION: | 80.0% NaCl, 5.0% NaCMC 7H4F, 14.25% Povidone, 0.75% Magnesium Stearate. |
| TABLET WEIGHT: | 0.0841 g. |
| TABLET HEIGHT: | 0.247 in. |
| COMPRESSION: | 500 lb. |

| Tablet No. | Tablet Weight (g) | Tablet Height (in) |
|---|---|---|
| 1 | 0.0955 | 0.309 |
| 2 | 0.0877 | 0.284 |
| 3 | 0.0848 | 0.273 |
| 4 | 0.0914 | 0.294 |
| 5 | 0.0825 | 0.265 |
| Average | 0.0884 | 0.385 |

PROCEDURE:

1. Lubricate large flanched piston with medical fluid 100cs CODE 80036 CONTROL 258887
2. Prime capsule (membrane end).
3. Insert large flanched piston into Hoechst Celanese capsule using the piston inserted.
4. Push piston up & down using a rod.
5. Insert osmotic engine tablet into capsule from the membrane end and push engine tablet down.
6. Insert half way the membrane plug.
7. Add two drops of glue in each side of membrane plug.
8. Press all the way down membrane plug and wipe glue residue with a paper towel.
9. Add beneficial agent into capsule almost all the way to the top.
10. Insert orifice.
11. Insert orifice half way and add two drops of glue in each side of orifice plug (all orifices were glued except systems 26–30).

COMPONENTS:

| | |
|---|---|
| Formulation #1: | 1% blue dye in deionized water |
| Membrane: | Fast "K" 100% hytrel 8171 |
| Engine Tablet: | 80.0% NaCl, 5.0% NaCMC 7H4F, 14.25% Povidone, 0.75% Magnesium Stearate. |
| Piston: | Large santoprene flanched |
| Orifice: | 1–5 screw spiral |
| Orifice: | 11–15 external flow moderator (Figure 3) |
| Orifice: | 21–25 internal 1 mm duckbill (Figure 2) |

As shown in FIG. 4, the release rate of the delivery devices of FIGS. 2 and 3 having the slit orifices is significantly more constant than the release rate of the delivery device having a spiral shaped flow moderator. This characteristic is of course very important when the delivery device is used to supply drugs to humans over an extended period of time. The slit orifice may be used to alter the start-up beneficial agent delivery profile by changing the pressure at which the orifice opens and/or decreasing the initial diffusive burst from the flow modulator.

In assembling the delivery device of the present invention, the beneficial agent may also be added with the capsule after the orifice has been inserted into the capsule. In such an assembly, a needle is inserted through the orifice and into the capsule such that beneficial agent is delivered into the capsule via the needle. This technique is advantageous because the slit orifice allows air to escape the capsule as the beneficial agent fills the capsule. Thus, after the delivery device is inserted into the environment of use, the osmotic agent need not compress any air bubbles in the beneficial agent which would ordinarily delay start-up of beneficial agent delivery.

Figure 5:
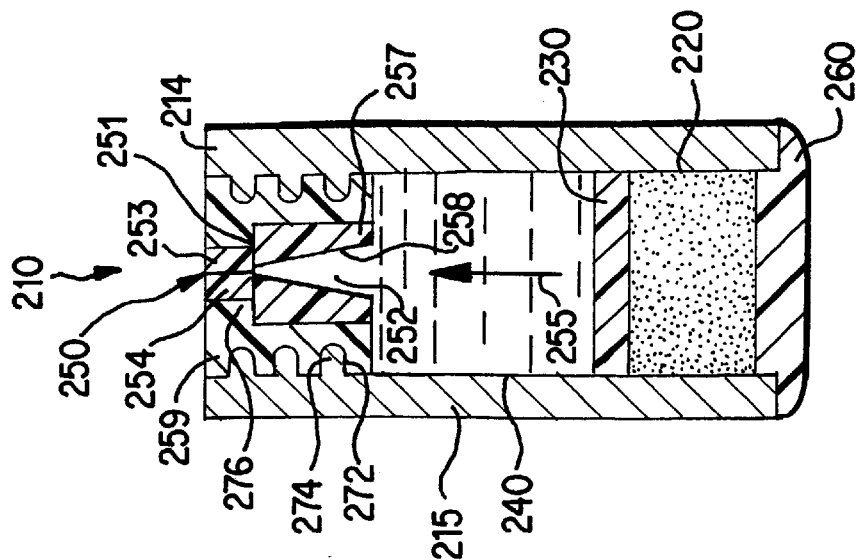
FIG. 5 illustrates a delivery device which includes a slit orifice and a conical recess according to another embodiment of the invention.

FIG. 5 illustrates another embodiment of the invention which includes a mechanism for varying the pressure required to open the orifice. As shown in FIG. 5, the orifice 250 is located at the outlet end 214 of a capsule 215. The delivery device 210 also includes a membrane 260, a first chamber 220 containing an osmotic agent, a second chamber 240 containing a beneficial agent, and a moveable piston 230 separating the first chamber 220 from the second chamber 240. The membrane 260, osmotic agent, piston 230, and second chamber 240 form an osmotic pump which functions as described above with respect to FIGS. 2 and 3.

The orifice 250, according to an exemplary embodiment, comprises three sections. A first portion 257 is located between the slit 254 and the second chamber 240 and is in fluid communication with both. A second portion 253 contains the slit 254. A third portion 259 occupies the annular space between the first and second portions and the inner wall of the capsule 215.

The slit 254 is housed in the second portion 253. The second portion is generally cylindrical in shape and preferably is formed of an elastic or semi-elastic material such as silicone, rubber, santoprene, polyurethane, etc. The elasticity of the second portion 253 allows the slit 254 to open under pressure from the beneficial agent.

Upstream of the slit 254 and second portion 253 is the first portion 257. The first portion 257 is also generally cylindrical in shape and has an inner recess 252. The outer radius of the first portion 257 may be greater than the outer radius of the second portion 253 so that a shoulder 251 is formed to secure the first and second portions in the delivery device 210. The first and second portions may be integrally formed as a single piece of material.

According to a preferred embodiment, the inner recess 252 of the first portion 257 has at least one wall 258 which is at an acute angle to the direction of flow 255 of the beneficial agent. Preferably, the inner recess 252 is in the shape of a cone so that its entire wall 258 is at an acute angle with respect to the direction of flow 255 of the beneficial agent. As the beneficial agent is forced into the inner recess 252, the beneficial agent exerts a force on the wall 258 of the inner recess 252 which has a radial component. The radial force operates to open the slit 254 in the second portion 253 of the orifice. Because the first and second portions are formed of an elastic or semi-elastic material, the force of the beneficial agent opens the slit 254 just wide enough to deliver the beneficial agent with very little if any forward diffusion of the beneficial agent or backward diffusion of external fluids into the second chamber 240.

The shape and composition of the first and second portions 257 and 253 and of the slit 254 may be adapted to accommodate beneficial agents of different viscosities or to adjust the pressure required to open the slit 254. For example, a beneficial agent with a relatively low viscosity will more easily flow through a smaller opening of the slit 254 than a beneficial agent with a higher viscosity. To equalize this discrepancy, the angle between the wall 258 and the direction of flow 255 can be adjusted for the viscous beneficial agent so that the slit is more easily opened. The angle between the wall 258 and the direction of flow 255 can also be adjusted to vary the pressure at which the slit will open and close for a beneficial agent of a given viscosity. In addition the dimensions and composition of the second portion 253 can be adjusted so that the slit 254 forms an orifice of a desired size under the operating parameters of the delivery device, e.g., the viscosity of the beneficial agent, the flow rate of the osmotic pump, and the pressure of the osmotic pump.

The third portion 259 occupies the annular space between the first and second portions and the inner wall of the capsule 215. The third portion 259 may have grooves 272 which mate with corresponding ridges 274 projecting from the inner wall of the capsule 215. The grooves 272 and ridges 274 may be circular or they may be in the form of screw threads such that the third portion 259 may be screwed into the outlet end of the capsule 215. The ridges and grooves are provided to secure the third portion 259 in the end of the capsule 215 in spite of the osmotic pressure generated by the osmotic pump.

The third portion 259 also includes an inwardly extending flange 276 which contacts the shoulder 251 formed between the first and second portions 257 and 253. The flange 276 contacts the shoulder 251 to retain the first and second portions in the capsule 215. The flange 276 may also function to apply a slight radial inward pressure on the second portion 253 so that the slit 254 remains closed in the absence of flow.

The orifice 250 provides the advantage that the flow channel may be significantly smaller than is required in a fixed diameter orifice, since the flow channel opens just large enough to deliver the beneficial agent. In addition, in the event that a suspended particle becomes lodged in the orifice 250, a new flow path is created around the obstacle. The orifice 250 is also very compact, as illustrated in FIG. 5.

Figure 6:
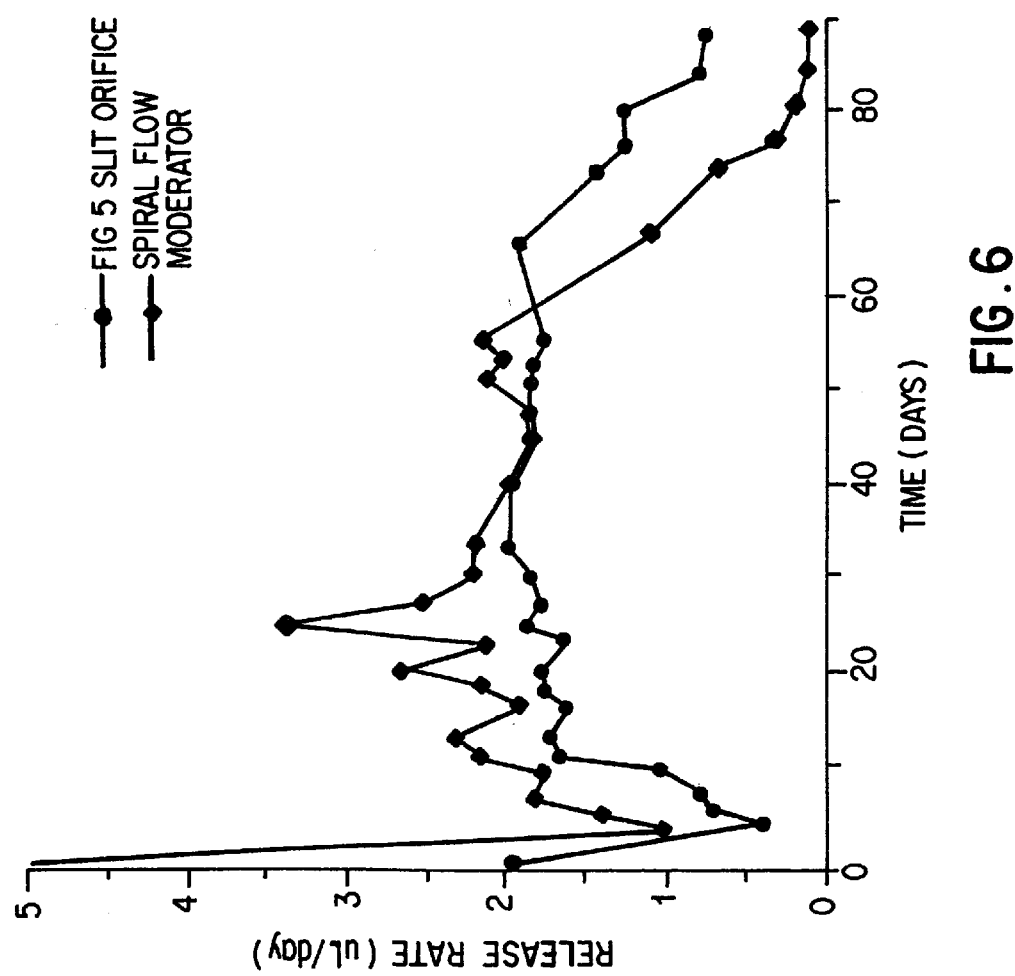
FIG. 6 is a graph which shows the release rate of the delivery device of FIG. 5 as a function of time.

The improved performance of the exemplary delivery device of FIG. 5 is shown in FIG. 6. FIG. 6 is a graph of the release rate in microliters per day over time of the delivery device of FIG. 5. FIG. 6 also shows the release rate of a delivery device having a flow moderator orifice in the shape of a spiral. The data used in FIG. 6 were obtained by placing each delivery device in a release rate bath. The delivery devices were filled with a 1% solution of blue dye in deionized water. At fixed points in time, measurements were taken of the concentration of blue dye in the release rate bath.

As shown in FIG. 6, the release rate of the delivery devices of FIG. 5 having the slit orifice is significantly more constant than the release rate of the delivery device having a spiral shaped flow moderator.

Figure 7:
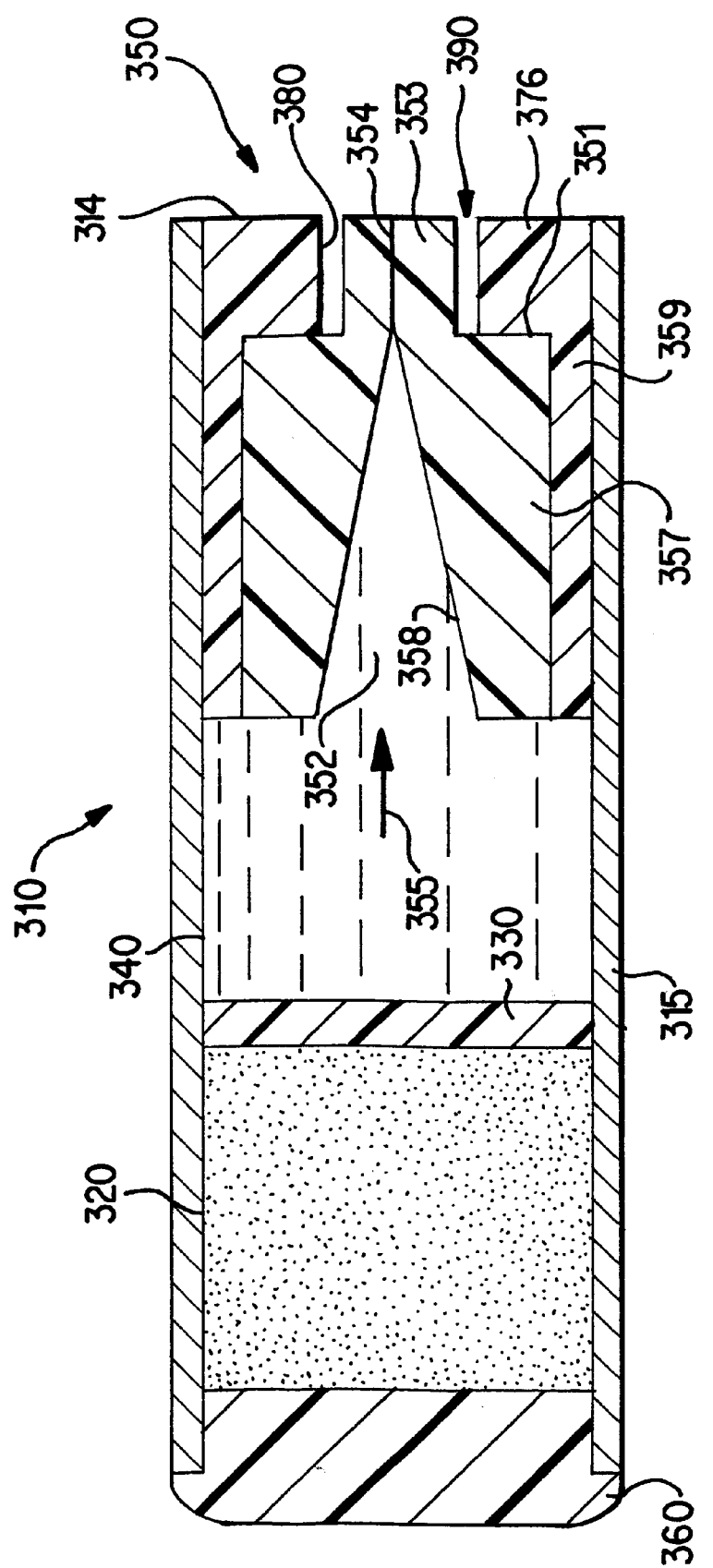
FIG. 7 illustrates a delivery device which includes a slit orifice and a rigid inner cylindrical member according to another embodiment of the invention.

FIG. 7 illustrates another embodiment of an orifice which includes an inner recess 352 and an inner cylindrical member 359. As shown in FIG. 7, the orifice 350 is located at the outlet end 314 of the capsule 315. The delivery device 310 also includes a membrane 360, a first chamber 320 containing an osmotic agent, a second chamber 340 containing a beneficial agent, and a moveable piston 330 separating the first chamber 320 from the second chamber 340. The membrane 360, osmotic agent, piston 330, and second chamber 340 form an osmotic pump which functions as described above with respect to FIGS. 2 and 3.

The orifice 350, according to an exemplary embodiment, comprises three components. A first portion 357 is located between the slit 354 and the second chamber 340 and is in fluid communication with both. A second portion 353 contains the slit 354. A third portion 359 resides in the annular space between the first and second portions and the inner wall of the capsule 315.

The slit 354 is housed in the second portion 353. The second portion is generally cylindrical in shape and preferably is formed of an elastic or semi-elastic material such as silicone, rubber, santoprene, polyurethane or an elastomeric thermoplastic polymer such as C-FLEX. The elasticity of the second portion 353 allows the slit 354 to open under pressure from the beneficial agent.

Upstream of the slit 354 and second portion 353 is the first portion 357. The first portion 357 is also generally cylindrical in shape and has an inner recess 352. The outer radius of the first portion 357 may be greater than the outer radius of the second portion 353 so that a shoulder 351 is formed to secure the first and second portions in the delivery device 310. The first and second portions may be integrally formed as a single piece of material.

According to a preferred embodiment, the inner recess 352 of the first portion 357 has at least one wall 358 which is at an acute angle to the direction of flow 355 of the beneficial agent. Preferably, the inner recess 352 is in the shape of a cone so that its entire wall 358 is at an acute angle with respect to the direction of flow 355 of the beneficial agent. As the beneficial agent is forced into the inner recess 352, the beneficial agent exerts a force on the wall 358 of the inner recess 352 which has a radial component. The radial force operates to open the slit 354 in the second portion 353 of the orifice. Because the first and second portions are formed of an elastic or semi-elastic material, the force of the beneficial agent opens the slit 354 just wide enough to deliver the beneficial agent with little if any forward diffusion of the beneficial agent or backward diffusion of external fluids into the second chamber 340. The shape of the inner recess 352 (e.g., the angle of the wall 358) may be adapted to accommodate beneficial agents of different viscosities or to adjust the pressure required to open the slit 354. In addition, the dimensions and composition of the second portion 353 can be chosen so that the slit 354 forms an orifice of a desired size under the operating parameters of the delivery device, e.g., the viscosity of the beneficial agent, the flow rate of the osmotic pump, and the pressure of the osmotic pump.

The third portion 359 resides in the annular space between the first and second portions and the inner wall of the capsule 315. The third portion 359 is preferably formed of a rigid material such as titanium. The third portion may be generally in the form of an inner cylindrical member or "cup" with a hole 380 in its bottom. The third portion 359 is preferably formed to have an outer diameter which is small enough that the third portion 359 may be pressed into the outlet end 314 of the capsule 315. The outer diameter of the third portion 359 is preferably large enough, however, that the third portion 359 is frictionally retained in the outlet end 314 of the capsule 315 in the presence of the osmotic pressure generated by the osmotic pump. When properly dimensioned, the frictional force between the third portion 359 and the capsule 315 is sufficient to permanently retain the third portion 359 in the capsule 315.

The third portion 359 also includes an inwardly extending flange 376 which contacts the shoulder 351 formed between the first and second portions 357 and 353. The flange 376 contacts the shoulder 351 to retain the first and second portions in the capsule 315. The flange 376 preferably does not extend all the way inward to the second portion 353 so that a gap 390 exists between the second portion containing the slit 354 and the flange 376. The gap 390 is provided so that the flange 376 does not exert any pressure on the slit 354.

The orifice 350 provides the advantages that the flow channel which opens under pressure from the beneficial agent may be significantly smaller than is required in a fixed diameter orifice, since the flow channel opens just large enough to deliver the beneficial agent. In addition, in the event that a suspended particle becomes lodged in the orifice 350, a new flow path is created around the obstacle. The rigid third portion 359 is also very effective in maintaining the orifice 350 in the capsule against the osmotic pressure. The orifice is also very compact, which is advantageous for subcutaneous implantation.

Figure 8:
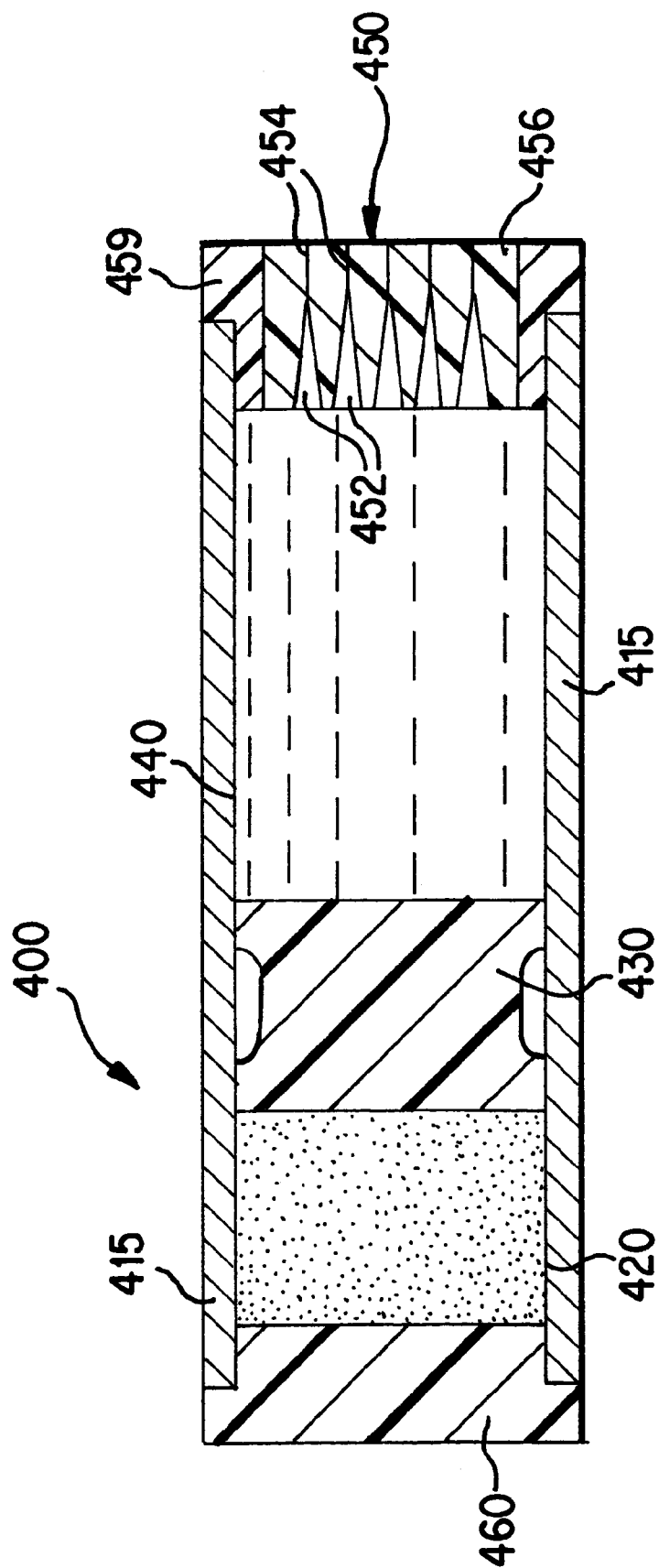
FIG. 8 illustrates a delivery device which includes a plurality of slit orifices according to another embodiment of the present invention.

FIG. 8 illustrates another embodiment of an orifice 450 which includes a plurality of slit orifices 454. As shown in FIG. 8, the orifice 450 is located at the outlet end of the capsule 415. The delivery device 400 also includes a membrane 460, a first chamber 420 containing an osmotic agent, a second chamber 440 containing a beneficial agent, and a movable piston 430 separating the first chamber 420 from the second chamber 440. The membrane 460, osmotic agent, piston 430, and second chamber 440 form an osmotic pump which functions as described above with respect to FIGS. 2 and 3.

The orifice 450, according to an exemplary embodiment, includes a plurality of slit orifices similar to those described above in reference to FIGS. 2, 5, and 7. As shown in FIG. 8, an inner cylindrical member 459 is positioned in the end of the capsule 415 opposite the membrane 460. In this embodiment, a flexible member 456, which contains the plurality of slit orifices 454 and inner recesses 452, has been prepositioned in the inner cylindrical member 459. Similar to the embodiment depicted in FIG. 5, the inner cylindrical member 459 may be made of a material which helps maintain the seal between the capsule 415 and the orifice 450. For example, the inner cylindrical member 459 may be made of less resilient material than the flexible member 456 which contains the plurality of slits 454. In another embodiment of the present invention not depicted, the inner cylindrical member 459 is not included, and the flexible member 456 is adapted and configured to form a seal with the capsule 415.

As illustrated in FIG. 8, the orifice 450 includes a plurality of slit orifices 454 and inner recesses 452, which are particularly useful for delivering beneficial agents having suspensions of bioactive macromolecules such as proteins and genes. Known delivery orifices may cause such suspension formation to separate as the formulation is moved into a small chamber such as a helical orifice prior to being released into the environment of use. The embodiment of the present invention which incorporates a plurality of slit orifices 454 allows such suspension formulations to travel relatively unrestricted, minimizing the amount of separation before it exits the delivery device 400. In this regard, the plurality of slit orifices 454 in combination with the plurality of inner recesses 452 allows for a nearly constant front of beneficial agent, such as suspensions containing bioactive macromolecules, to be released from the delivery device 400, while also minimizing back diffusion of external fluids into the delivery device. Furthermore, the embodiment of the present invention illustrated in FIG. 8 also provides the many advantages described above in reference to FIGS. 1–7.

In the event that one or some of the slit orifices 454 becomes clogged with macromolecules or particles, the other non-clogged slit orifices of the delivery device 400 will continue to release the beneficial agent. Thus, the plurality of slits 454 and recesses 452 acts as a safety, ensuring that beneficial agent delivery continues.

Materials which may be used for the capsule should be sufficiently strong to ensure that the capsule will not leak, crack, break, or distort under stresses to which they would be subjected during implantation or under stresses due to the pressures generated during operation. The capsule may be formed of chemically inert and biocompatible, natural or synthetic materials which are known in the art. The material of the capsule is preferably a non-bioerodible material which remains in the patient after use, such as titanium. However, the material of the capsule may alternatively be of bioerodible material which bioerodes in the environment after dispensing of the beneficial agent. Generally, preferred materials for the capsule are those acceptable for human implants.

In general, typical materials of construction suitable for the capsule according to the present invention include non-reactive polymers or biocompatible metals or alloys. The polymers include acrylonitrile polymers such as acrylonitrile-butadiene-styrene terpolymer, and the like; halogenated polymers such as polytetrafluoroethylene, polychlorotrifluoroethylene, copolymer of tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene; and the like. Metallic materials useful for the capsule include stainless steel, titanium, platinum, tantalum, gold, and their alloys, as well as gold-plated ferrous alloys, platinum-plated ferrous alloys, cobalt-chromium alloys and titanium nitride coated stainless steel.

In general, materials suitable for use in the piston are elastomeric materials including the non-reactive polymers listed above, as well as elastomers in general, such as polyurethanes and polyamides, chlorinated rubbers, styrene-butadiene rubbers, and chloroprene rubbers.

The osmotic tablet is an osmotic agent which is a fluid-attracting agent used to drive the flow of the beneficial agent. The osmotic agent may be an osmagent, an osmopolymer, or a mixture of the two. Species which fall within the category of osmagent, i.e., the non-volatile species which are soluble in water and create the osmotic gradient driving the osmotic inflow of water, vary widely. Examples are well known in the art and include magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species.

Species which fall within the category of osmopolymer are hydrophilic polymers that swell upon contact with water, and these vary widely as well. Osmopolymers may be of plant or animal origin, or synthetic, and examples of osmopolymers are well known in the art. Examples include: poly(hydroxy-allyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross-linked with glyoxal, formaldehyde or glutaraldehyde and having a degree of polymerization of 200 to 30,000, a mixture of methyl cellulose, cross-linked agar and carboxymethylcellulose, a mixture of hydroxypropyl methylcellulose and sodium carboxymethylcellulose, polymers of N-vinyllactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross-linked indene-maleic anhydride polymers, Good-Rite polyacrylic acids having molecular weights of 80,000 to 200,000, Polyox polyethylene oxide polymers having molecular weights of 100,000 to 5,000,000, starch graft copolymers, and Aqua-Keeps acrylate polymer polysaccharides.

Delivery capsules in accordance with the present invention for the delivery of beneficial agents, may be manufactured by a variety of techniques, many of which are known in the art.

In one such embodiment of this invention, the beneficial agents contained in the second chamber are flowable compositions such as liquids, suspension, or slurries, and are poured into the capsule after the osmotic agent and the piston have been inserted. Alternatively, such flowable compositions may be injected with a needle through a slit in the plug, which allows for filling without air bubbles. Still further alternatives may include any of the wide variety of techniques known in the art for forming capsules used in the pharmaceutical industry.

Animals to whom drugs may be administered using systems of this invention include humans and other animals. The invention is of particular interest for application to humans and household, sport, and farm animals, particularly mammals. For the administration of beneficial agents to animals, the devices of the present invention may be implanted subcutaneously or intraperitoneally or at any other location in a biological environment where aqueous body fluids are available to activate the osmotic engine.

The devices of this invention are also useful in environments outside of physiological or aqueous environments. For example, the devices may be used in intravenous systems (attached to an IV pump or bag or to an IV bottle, for example) for delivering beneficial agents to animals, primarily to humans. They may also be utilized in blood oxygenators, kidney dialysis and electrophoresis, for example. Additionally, devices of the present invention may be used in the biotechnology area, such as to deliver nutrients or growth regulating compounds to cell cultures.

The present invention applies to the administration of beneficial agents in general, which include any physiologically or pharmacologically active substance. The beneficial agent may be any of the agents which are known to be delivered to the body of a human or an animal such as drug agents, medicaments, vitamins, nutrients, or the like. The beneficial agent may also be an agent which is delivered to other types of aqueous environments such as pools, tanks, reservoirs, and the like. Included among the types of agents which meet this description are biocides, sterilization agents, nutrients, vitamins, food supplements, sex sterilants, fertility inhibitors and fertility promoters.

Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species.

Examples of drugs which may be delivered by devices according to this invention include, but are not limited to prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, prolactin, somatostatin, lypressin, pancreozymin, luteinizing hormone, LHRH, LHRH agonists and antagonists, leuprolide, interferons, interleukins, growth hormones such as human growth hormone, bovine growth hormone and porcine growth hormone, fertility inhibitors such as the prostaglandins, fertility promoters, growth factors, coagulation factors, human pancreas hormone releasing factor, analogs and derivatives of these compounds, and pharmaceutically acceptable salts of these compounds, or their analogs or derivatives.

The beneficial agent can be present in this invention in a wide variety of chemical and physical forms, such as solids, liquids and slurries. On the molecular level, the various forms may include uncharged molecules, molecular complexes, and pharmaceutically acceptable acid addition and base addition salts such as hydrochlorides, hydrobromides, sulfate, laurylate, oleate, and salicylate. For acidic compounds, salts of metals, amines or organic cations may be used. Derivatives such as esters, ethers and amides can also be used. An active agent can be used alone or mixed with other active agents.

According to other embodiments of the present invention, the delivery device may take different forms. For example, the piston may be replaced with a flexible member such as a diaphragm, partition, pad, flat sheet, spheroid, or rigid metal alloy, and may be made of any number of inert materials. Furthermore, the osmotic device may function without the piston, having simply an interface between the osmotic agent/fluid additive and the beneficial agent.

The above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention as defined by the following claims.

What is claimed is:

1. A method of forming a delivery device comprising the steps of:

filling a chamber of the delivery device with a beneficial agent having a known viscosity;

providing an exit passage through which the beneficial agent is delivered, the exit passage comprising a first portion having a wall which is at an angle to a direction of flow of the beneficial agent, the exit passage also comprising a slit orifice downstream of the first portion; and selecting the angle of the wall with respect to the direction of flow of the beneficial agent based on the viscosity of the beneficial agent so that the force of the flow of the beneficial agent opens the slit orifice to deliver the beneficial agent substantially without diffusion of external liquids into the chamber.

2. The method of claim 1, further comprising the step of forming the first portion of the exit passage in the shape of a cone with the slit orifice intersecting an apex of the cone.

3. A method of forming a delivery device comprising:

inserting a beneficial agent into a capsule;

locating an osmotic agent in the capsule;

positioning a flexible member at least partially inside the capsule; and forming a slit orifice in the flexible member, the slit orifice being closed when a pressure of the beneficial agent in the capsule is less than a predetermined pressure and being opened when the pressure of the beneficial agent is greater than the predetermined pressure thereby permitting flow of the beneficial agent through the slit orifice and out of the capsule.

4. The method of claim 3, wherein the beneficial agent is inserted into the capsule after the flexible member has been positioned at least partially inside the capsule.

5. The method of claim 3, wherein the slit orifice in formed in said flexible member after the flexible member has been positioned at least partially inside the capsule.

6. The method of claim 3, wherein said forming of the slit orifice includes inserting at least one of a hypodermic needle, pin, or blade through at least a portion of the flexible member.

7. The method of claim 3, wherein the flexible member is positioned partially inside the capsule.

8. The method of claim 3, wherein the flexible member is positioned completely inside the capsule.

9. The method of claim 3, further comprising inserting a flow moderator at least partially inside the flexible member.

10. The method of claim 3, further comprising locating a member having an inner recess at least partially inside said enclosure.

11. The method of claim 10, further comprising locating the flexible member at least partially inside the inner recess of the member.

12. The method of claim 3, further comprising forming a plurality of slit orifices in the flexible member.

13. A method of forming an osmotic delivery system comprising:

locating a beneficial agent in a capsule;

providing an osmotic agent for applying osmotic pressure to the beneficial agent; and inserting a plug having a slit orifice at least partially into the capsule, the slit orifice being closed when a pressure of the beneficial agent is less than a predetermined pressure and being opened when the pressure of the beneficial agent is greater than the predetermined pressure thereby permitting flow of the beneficial agent through the slit orifice and out of the capsule.

14. The method of claim 13, further comprising forming the slit orifice in the plug.

15. The method of claim 13, further comprising inserting a piston into the capsule.

* * * * *

UNITED STATES PATENT AND TRADEMARK OFFICE
CERTIFICATE OF CORRECTION

PATENT NO. : 6,217,906 B1  Page 1 of 1
DATED : April 17, 2001
INVENTOR(S) : Juan C. Gumucio et al.

It is certified that error appears in the above-identified patent and that said Letters Patent is hereby corrected as shown below:

<u>Column 18,</u>
Line 56, replace "in" with -- is --.

Signed and Sealed this

Eighth Day of January, 2002

Attest:

JAMES E. ROGAN
Attesting Officer    Director of the United States Patent and Trademark Office